US011479801B2

(12) United States Patent
Albrecht et al.

(10) Patent No.: US 11,479,801 B2
(45) Date of Patent: Oct. 25, 2022

(54) BIOLOGIC MACHINES FOR THE DETECTION OF BIOMOLECULES

(71) Applicant: Laboratory Corporation of America Holdings, Burlington, NC (US)

(72) Inventors: Jeff Albrecht, Los Angeles, CA (US); Andrew J. Conrad, Malibu, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 364 days.

(21) Appl. No.: 16/857,353

(22) Filed: Apr. 24, 2020

(65) Prior Publication Data

US 2020/0248225 A1    Aug. 6, 2020

Related U.S. Application Data

(62) Division of application No. 13/772,514, filed on Feb. 21, 2013, now Pat. No. 10,662,459.

(60) Provisional application No. 61/661,059, filed on Jun. 18, 2012, provisional application No. 61/614,645, filed on Mar. 23, 2012.

(51) Int. Cl.
*C12Q 1/00* (2006.01)
*C12Q 1/04* (2006.01)
*G01N 33/569* (2006.01)

(52) U.S. Cl.
CPC ............. *C12Q 1/04* (2013.01); *G01N 33/569* (2013.01); *G01N 33/56983* (2013.01)

(58) Field of Classification Search
CPC ....................................................... C12Q 1/04
See application file for complete search history.

(56) References Cited

U.S. PATENT DOCUMENTS

| | | | |
|---|---|---|---|
| 10,662,459 | B2 | 5/2020 | Albrecht et al. |
| 2004/0137532 | A1 | 7/2004 | Szabo et al. |
| 2004/0224359 | A1 | 11/2004 | Madonna et al. |
| 2005/0003346 | A1 | 1/2005 | Voorhees et al. |
| 2005/0153368 | A1 | 7/2005 | Zwiebel |
| 2005/0250096 | A1 | 11/2005 | Wheeler et al. |
| 2006/0024054 | A1 | 2/2006 | Moriyama |
| 2006/0240541 | A1 | 10/2006 | Petruno et al. |
| 2007/0048745 | A1 | 3/2007 | Joyce et al. |
| 2009/0136948 | A1 | 5/2009 | Han et al. |
| 2009/0258341 | A1 | 10/2009 | Voorhees et al. |
| 2009/0286225 | A1 | 11/2009 | Wheeler et al. |
| 2010/0112549 | A1 | 5/2010 | Rey et al. |
| 2013/0252231 | A1 | 9/2013 | Albrecht et al. |

FOREIGN PATENT DOCUMENTS

| | | |
|---|---|---|
| EP | 2828411 | 1/2015 |
| HK | 1205763 | 7/2018 |
| WO | 2013142003 | 9/2013 |

OTHER PUBLICATIONS

Blasco, R. et al., "Specific assays for bacteria using phage mediated release of adenylate kinase," J. Appl. Microbiol. 84:661-666 (1998).
CA 2,867,288, Office Action, dated Nov. 30, 2021, 4 pages.
CA2,867,288 , "Office Action", dated Oct. 10, 2019, 3 pages.
EP13764898.6 , "Extended European Search Report", dated Mar. 14, 2016, 12 pages.
EP13764898.6 , "Supplementary European Search Report", dated Nov. 2, 2015, 4 pages.
Ivnitski et al., "Biosensors for Detection of Pathogenic Bacteria", Biosensors and Bioelectronics, vol. 14, No. 7, Oct. 1, 1999, pp. 599-624.
PCT/US13/27002 , "International Search Report and Written Opinion", dated Jul. 12, 2013, 18 pages.
Schlessinger et al., "Antigen-indiced conformational changes in antibodies and their Fab fragments studied by polarization of fluorescence", Proceedings of the National Academy of Sciences of the United States of America PNAS USA Section , Mmunologycommunicated by Herman N. Eisen, vol. 72, Jul. 1, 1975, pp. 2775-2779.
Steinberg et al., "Sensitive Instrument for the Study of Circular Polarization of Luminescence", Review of Scientific Instruments (American Institute of Physics College Park, MD 20740 USA), val. 43, No. 3, Jan. 1, 1972, pp. 409-413.
U.S. Appl. No. 13/772,514, Final Office Action, dated Jun. 6, 2019, 12 pages.
U.S. Appl. No. 13/772,514, Final Office Action, dated Oct. 31, 2017, 13 pages.
U.S. Appl. No. 13/772,514, Final Office Action, dated Jul. 22, 2016, 17 pages.
U.S. Appl. No. 13/772,514, Non-Final Office Action, dated Dec. 18, 2015, 10 pages.
U.S. Appl. No. 13/772,514, Non-Final Office Action, dated Dec. 17, 2018, 13 pages.
U.S. Appl. No. 13/772,514, Non-Final Office Action, dated Apr. 6, 2017, 14 pages.
CA Application No. 2,867,288, Office Action, dated Aug. 21, 2020, 3 pages.
CA Application No. 2,867,288, Office Action, dated Oct. 3, 2018, 4 pages.
EP Application No. 13764898.6, Office Action, dated Nov. 24, 2016, 4 pages.
International Patent Application No. PCT/US13/27002, "Invitation to Pay Additional Fees and Partial Search Report Received", dated Apr. 17, 2013, 2 pages.
International Patent Application No. PCT/US13/27002, Search Report and Written Opinion of the International Searching Authority, dated Jul. 12, 2013, 13 pages.

*Primary Examiner* — Albert M Navarro
(74) *Attorney, Agent, or Firm* — Kilpatrick Townsend & Stockton LLP

(57) ABSTRACT

Disclosed are methods, devices and systems for the isolation and detection of biomolecules from a sample. The embodiments, detection of such biomolecules provides for detection of microorganisms. For example, disclosed are methods, devices and systems that use bacteriophage-based amplification of the signal in detection of bacteria and other microorganisms. The devices, systems and methods of the invention may allow for the detection of certain biomolecules peptides and ions in real time using minute amounts of sample.

21 Claims, 8 Drawing Sheets

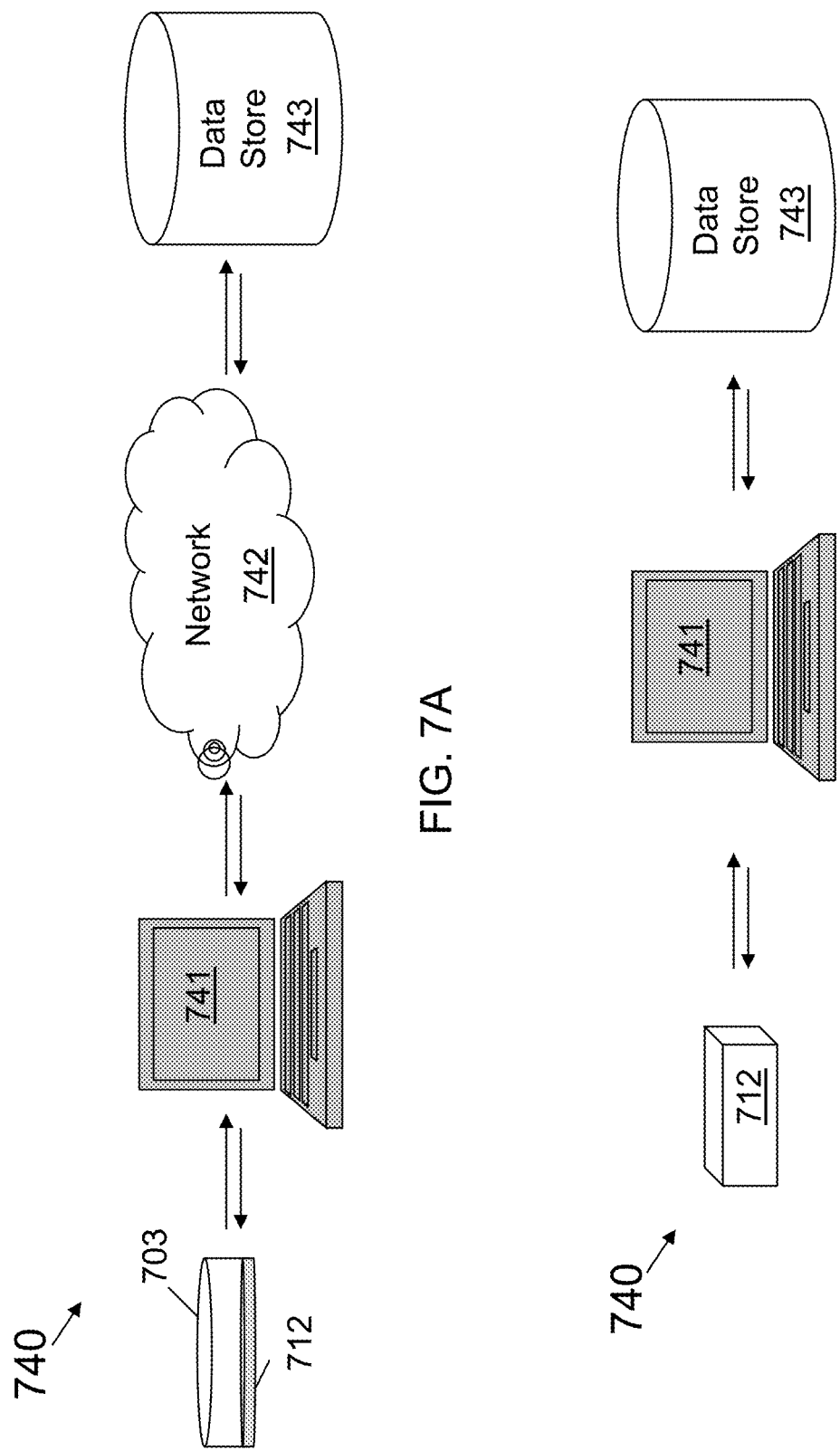

BIOLOGIC MACHINES FOR THE DETECTION OF BIOMOLECULES

This application is a divisional application of U.S. patent application Ser. No. 13/772,514, filed Feb. 21, 2013, which claims priority to U.S. Provisional Patent Application 61/614,645 filed Mar. 23, 2012 and U.S. Provisional Patent Application 61/661,059 filed Jun. 18, 2012. The disclosures of U.S. patent application Ser. No. 13/772,514, and U.S. Provisional Patent Applications 61/614,645 and 61/661,059 are incorporated by reference in their entireties herein.

FIELD OF THE INVENTION

This invention relates to biologic machines for the detection of microorgansims and biomolecules within microorganisms.

BACKGROUND

There is a strong interest in the detection of microorganisms such as bacteria and other microorganisms in both biological and food based samples. Bacterial pathogens can cause substantial morbidity among humans and domestic animals, as well as immense economic loss. Also, detection of microorganisms is a high priority within the Food and Drug Administration (FDA) given outbreaks of life-threatening or fatal illness caused by ingestion of food contaminated with certain microorganisms e.g., *Escherichia coli* or *Salmonella* spp.

Traditional microbiological tests for the detection of bacteria and viruses rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving immunoassays or gene probes generally require an enrichment step in order to obtain adequate sensitivity. Polymerase chain reaction (PCR) tests also include an amplification step and therefore are capable of both very high sensitivity and selectivity. However, the sample size that can be economically subjected to PCR testing is limited. With dilute bacterial suspensions, most small subsamples will be free of cells and therefore enrichment steps are still required. The time required for biological enrichment is dictated by the growth rate of the target bacterial population of the sample, by the effect of the sample matrix, and by the required sensitivity. For instance, a magnetic-capture PCR system for verotoxigenic *E. coli* can require about 5, 7, and 10 hours enrichment to detect 1000, 100, and 1 colony forming unit per milliliter (cfu/ml), respectively, in a model system, and 15 hours enrichment to detect 1 cfu per gram (g) in ground beef. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water (or other product) may have made its way into livestock or humans. In addition, increases in antibiotic-resistant bacteria and biodefense considerations make rapid identification of bacterial pathogens in water, food, and clinical samples critical priorities worldwide.

Also, there is a strong interest in the detection of the levels of metabolites and other biomolecules. Such biomolecules may be derived from microorganisms of interest. Assays for protein biomolecules may utilize antibodies that recognize the protein of interest. Or, assays for detection of peptides or non-protein biomolecules may involve partial purification and chemical analysis using systems such as chromatography and mass spectrometry. Or, nucleic acid probes may be used to detect levels of mRNA in a sample.

Generally, however, such methods may take up to several days and/or require a significant amount of a material. For example, techniques involving immunoassays or gene probes generally require an enrichment step in order to obtain adequate sensitivity. Polymerase chain reaction (PCR) tests include an amplification step to obtain very high sensitivity and selectivity. Also, the sample size that can be economically subjected to PCR testing is limited.

Therefore, there is a need for more rapid, simple, and sensitive detection and identification of microorganisms, such as bacteria and other potentially pathogenic microorganisms. There is also a need for direct, rapid, simple, and sensitive detection and identification of biomolecules that may be of clinical relevance.

SUMMARY OF THE INVENTION

Embodiments of the present invention relate to methods and systems for detection of microorganisms and biomolecules derived therefrom. The invention may be embodied in a variety of ways.

For example, in certain embodiments, the invention comprises methods for detecting a microorganism or a biomolecule derived therefrom. The method may comprising the steps of: infecting the isolated microorganism with an infectious agent that can reproduce in the microorganism so as to produce progeny infectious agents; allowing the infected microorganism to release the progeny infectious agents; and detecting the progeny infectious agents, wherein detection of the progeny infectious agents indicates that the microorganism is present in the sample.

In other embodiments, the invention comprises devices and systems for detecting a microorganism. The system may comprise: a component for containing a sample comprising a microorganism; a component for adding an infectious agent that can infect the microorganism so as to generate progeny infectious agents; and a component for detecting the progeny infectious agents, wherein detection of the infectious agents indicates that the microorganism is present in the sample.

Also, in some embodiments, the invention comprises a device and systems for detection of a biomolecule. For example, the biomolecule may be from a microorganism of interest. The device may comprise a container for holding at least one recognition partner for the biomolecule, wherein the recognition partner undergoes a measurable physical or chemical transformation upon interaction with the biomolecule. The device may also comprise a unit that detects the measurable physical or chemical transformation. In other embodiments, the device may be coupled (i.e., directly or remotely) to a computer. In other embodiments, the invention may comprise methods for detection of biomolecules using the devices and/or systems of the invention.

Each of the embodiments of the methods and systems of the invention can be applied to detection and quantification of a variety of microorganisms, including bacterial cells or other pathogens. The methods and systems of the present invention provide high detection sensitivity in a short time without the need for traditional biological enrichment. For example, embodiments of the present invention can provide for the detection and quantification of a single microorganism (e.g., bacterial cell) in a sample.

BRIEF DESCRIPTION OF THE FIGURES

The present invention may be better understood by reference to the following non-limiting figures.

FIGS. 7A and 7B illustrate system diagrams depicting exemplary computing devices in exemplary computing environments according to various embodiments of the invention.

DETAILED DESCRIPTION OF THE INVENTION

Definitions

Figure 1:
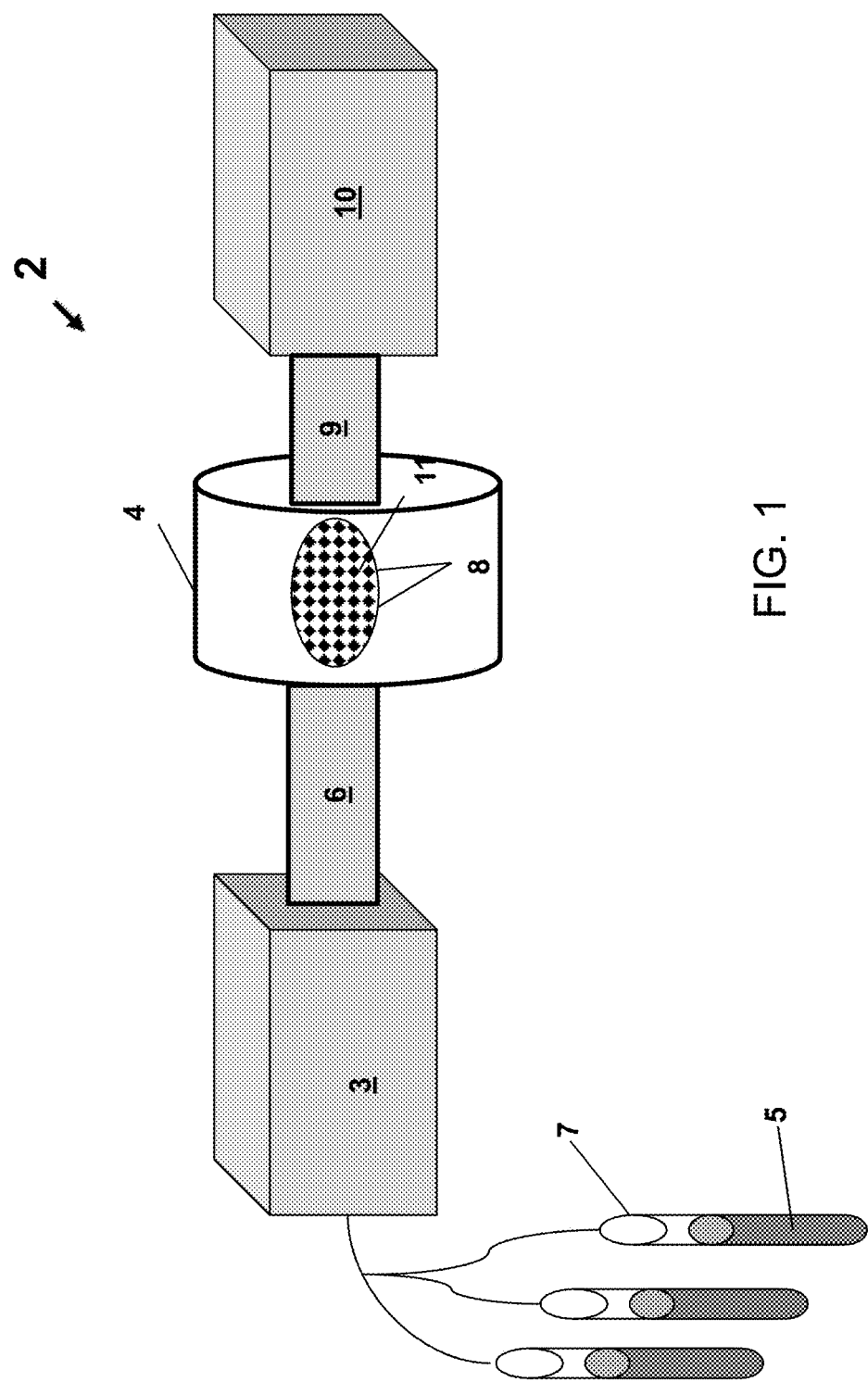
FIG. 1 illustrates a system for measuring bacteriophage in accordance with an embodiment of the invention.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate onto which biomolecules may be bound. For example, a solid support may be an assay well (i.e., such as a microtiter plate), or the solid support may be a location on an array, or a mobile support, such as a bead.

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like.

The term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent.

As used herein, an "analyte" refers to a molecule or compound that is being measured. The analyte may interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" refers to a molecule that can be measured in a quantitative assay. For example, a detectable moiety may comprise an enzyme that may be used to convert a substrate to a product that can be measured (e.g., a visible substrate). Or, a detectable moiety may be a radioisotope that can be quantified. Or, a detectable moiety may be a fluorophore or a luminescent molecule. Or, other detectable molecules may be used.

As used herein, the term "equivalence zone" indicates the region in a precipitin reaction in which the concentration of antigen and antibody leads to maximal precipitation. Thus, if either antigen or antibody are in excess, precipitation does not occur.

As used herein, "bacteriophage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasmas, protozoa, yeasts, and other microscopic living organisms and uses them to replicate itself. Here, "microscopic" means that the largest dimension is one millimeter or less. Bacteriophage are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification. The term "bacteriophages" is used to refer to bacteriophages in general or multiple strains; the term "bacteriophage" is used to refer to multiple copies of virus particles of the same strain.

As used herein, a "bacteriophage marker" is any biological or organic element that can be associated with the presence of bacteriophage. Without limitation, this may be the bacteriophage itself; a protein or other molecule incorporated into the phage structure; a protein associated with, or gene product engineered into, the bacteriophage; RNA or DNA associated with the bacteriophage; or any portion of any of the foregoing. As used herein a "bacterial marker" is any biological or organic element that can be used to identify the presence of a bacterium such as constituents released when a bacterium is lysed by a bacteriophage, including cell wall components, bacterial nucleic acids, proteins, enzymes, small molecules, or any portion of the foregoing. For example, in certain embodiments, luciferase protein incorporated into a structural component of the phage (e.g., fusion with the capsid protein) or as a soluble protein is a bacteriophage marker.

As used herein, the term "biomolecule" includes, but is not limited to, biological molecules such as amino acids, fatty acids, peptides, and polypeptides or proteins. The term "biomolecule" also refers to various compounds commonly present in mammalian species, including but not limited to, peptides such as insulin; metabolites such as glucose, vanillyl mandelic acid, and the like; neurotransmitters such as serotonin, dopamine, glutamate, or glutamic acid; or ions such as potassium, sodium, chromium or the like; or other biomolecules.

As used herein the term "biological sample" is used to refer to any fluid or tissue that can be isolated from an individual. For example, a biological sample may be whole blood, plasma, serum, other blood fraction, urine, cerebrospinal fluid, tissue homogenate, saliva, amniotic fluid, bile, mucus, peritoneal fluid, lymphatic fluid, perspiration, tissues, tissue homogenate, and the like.

As used herein, the term "recognition partner" refers to a molecule that can specifically and selectively recognize and interact with a second (i.e., different) molecule of interest. The interaction may be non-covalent, for example, as a result of hydrogen-bonding, van der Waals interactions, or electrostatic or hydrophobic interactions, or it may be covalent. As described in detail herein, the interaction may lead to a physical or chemical transformation of one of the molecules or both of the molecules (e.g., a conformational change). Or, the interaction may lead to a physical or chemical transformation of the environment as for example, the generation of an action potential.

Methods and Systems for Detection of Microorganisms

In one aspect, the present invention utilizes the biology of microorganisms for detection of a microorganism in a sample. Thus, embodiments of the invention rely on the amplification of a signal that may be provided upon infection of a microorganism with an infectious agent by the growth and replication of numerous progeny infectious agents.

A variety of microorganisms can be detected using the methods and systems described herein. In certain embodiments, the invention provides methods and systems for an ultrasensitive bacteriophage-based assay for the rapid detection and quantification of bacterial pathogens. In one embodiment, the present invention comprises methods and systems for detection of bacteriophage that are released from bacteria isolated from a biological sample.

For example, in certain embodiments, the invention may comprise method for detecting a microorganism. The method may comprise the steps of infecting the isolated microorganism with an infectious agent that can reproduce in the microorganism so as to produce progeny infectious agents; allowing the infected microorganism to release the progeny infectious agents; and detecting the progeny infectious agents, wherein detection of the progeny infectious agents indicates that the microorganism is present in the sample.

In an embodiment, the progeny infectious agents comprise a component that allows for detection. For example, the detectable component may comprise a detectable biomolecule. Or, the step of detecting the progeny infectious agents may comprise immunodetection of the infectious agent.

In certain embodiments, the method may comprise the step of introducing the infectious agents into the sample so as to infect the microorganism. Thus, in certain embodiments, the method utilizes a device comprising a component for introducing the infectious agent into a microorganism of interest. The component may comprise a plurality of pores, wherein the pore size allows the progeny infectious agents to pass through the pore, but does not allow the microorganism to pass out through the pore.

In certain embodiments, the method may comprise the step of separating the progeny infectious agents from the infected microorganism and/or other components in the sample. For example, in certain embodiments, the method may comprise a sized-based separation of the progeny infectious agents from the infected microorganism. In an embodiment, the separating may comprise filtration of the progeny infectious agents through a pore, wherein the pore size allows the progeny infectious agents to pass through the pore, but does not allow the microorganism to pass through the pore.

The method may also comprise the step of isolating any microorganisms that may be present in the sample from other components in the sample. For example, in an embodiment the method may comprise the step of isolating the microorgansim from other components in the sample by binding of the microorganism to a binding agent. In an embodiment, the binding agent may be bound to a solid support.

The methods of the invention may be used to assay samples for a variety of microorganisms. In certain embodiments, the microorganism is a bacteria and the infectious agent is a bacteriophage.

For example, in one embodiment, the invention may comprise a method for detecting a microorganism of interest comprising the steps of: isolating a bacterium from other components in the sample using bacteriophage immobilized in a first chamber; allowing the bacteriophage to infect the bacterium; lysing the bacterium to release progeny bacteriophage present in the bacterium in the first chamber; separating the progeny bacteriophage from the rest of the components in the mixture, as for example, via pores that allow the bacteriophage to exit the first chamber; and detecting the progeny bacteriophage, or a portion of the progeny bacteriophage, wherein detection of the progeny bacteriophage or a portion of the progeny bacteriophage (i.e., a bacteriophage marker), indicates that the bacterium is present in the sample. In this way, the progeny bacteriophage may be separated from the original phage used to infect the bacteria.

For example, in one embodiment, a biological sample containing bacteria is introduced into a chamber containing bacteriophage. Then bacteriophage are allowed to infect the bacteria in the sample such that during the infection, progeny bacteriophage are released. The sample comprising the bacteria, the bacteriophage used to infect the bacteria, and the progeny bacteriophage may be used for measurement of the progeny bacteriophage produced. If there is an increase in bacteriophage, this would be an indication that bacteria were present in the sample. The bacteriophage (i.e., progeny and initial bacteriophage) may be measured using a variety of detection techniques known in the art and as discussed in more detail herein.

In other embodiments, the invention comprises devices and systems to perform the methods of the invention. Thus, in certain embodiments, the invention may comprise a device or system for detecting a microorganism. The device or system may, in certain embodiments comprise: a component for containing a sample comprising a microorganism; a component for adding an infectious agent that can infect the microorganism so as to generate progeny infectious agents; and a component for detecting the progeny infectious agents, wherein detection of the infectious agents indicates that the microorganism is present in the sample.

In certain embodiments, the device or system may comprise a component for introducing the infectious agents into the sample so as to infect the microorganism. Thus, in certain embodiments, the component for introducing the infectious agent may comprise a plurality of pores, wherein the pore size allows the progeny infectious agents to pass through the pore, but does not allow the microorganism to pass out through the pore.

In certain embodiments, the device or system may comprise a component for separating the progeny infectious agents from the infected microorganism. For example, in an embodiment, the separating component may comprise a sized-based separation component. Thus, in certain embodiments, the separating component may comprise filtration of the progeny infectious agents through a pore, wherein the pore size allows the progeny infectious agents to pass through the pore, but does not allow the microorganism to pass through the pore.

The device or system may employ a variety of detectors to detect the progeny infectious agents. In an embodiment, the detection component may comprise a container for holding at least one recognition partner for the biomolecule, wherein the recognition partner undergoes a measurable physical or chemical transformation upon interaction with the biomolecule; and a unit that detects the measurable physical or chemical transformation. For example, in an embodiment, the detection component provides for visual detection of the progeny infectious agents, or detection of a label incorporated into the progeny infectious agents. Or, the detection component may provide for immunodetection of the infectious agent. Or, the detection component may provide an electrical or other quantifiable signal as discussed herein.

The device or system may also comprise a component for isolating any microorganisms that may be present in the sample from other components in the sample. For example, in an embodiment, the system may comprise a binding agent that recognizes and bind to the microorganism. In an embodiment, the binding agent may be bound to a solid support.

The devices or systems of the invention may be used to assay samples for a variety of microorganisms. In certain embodiments, the microorganism is a bacteria and the infectious agent is a bacteriophage.

For example, the device may comprise a chamber for containing bacteriophage that are used to infect bacteria of interest that may be in a sample. Also, the device may comprise a component that is used to separate the infecting bacteria from the progeny bacteriophages. In one embodiment, the component to separate the progeny bacteriophages may be a second chamber. In an embodiment, the second chamber may comprise a membrane with pores that are permeable to progeny bacteriophage released upon infection of a sample bacteria with an infecting bacteriophage. The device may also comprise a component for detecting the released progeny bacteriophage. The device may also comprise a component for transferring the sample into the device and/or through the device. For example, a transferring component in some embodiments may comprise a pump or some other device that transfers fluid.

For example, and as illustrated in FIG. 1, in one embodiment, a device or system of the invention 2 may be a flow-through type apparatus. In this way a biological samples (e.g., patient samples that potentially contain a microorganism of interest) may be processed in a continuous manner. The device or system may essentially comprise a flow-through system which allows for a microorganism present in the sample to be infected with an infectious agent that is specific to the sample and then any progeny infectious agent to be detected. For example, the microorganism being measured in the sample may be a bacterium and the infectious agent may be a bacteriophage.

Thus, as shown in FIG. 1, a sample 5 may be collected in a collection container 7, and then a pump 3 or other device used to transfer the sample into a first container 6. While the sample is in the first container 6, it may be mixed with an infectious agent that is specific to the microorganism of interest. For example, bacteria in the sample could be exposed to a bacteriophage that are contained in a medium in second outer container 4 having a membrane 8 that interfaces with the inner first container 6, the membrane 8 having pores 11 sized to let the bacteriophage through, but not let the bacteria in the sample out. The bacteriophage can then infect the bacteria in a very short time (e.g., about 20 minutes), and replicate to make numerous progeny bacteriophage. By including labeled precursor biomolecules (e.g., fluorescently labeled nucleotides, amino acids, or other biomolecules) the progeny bacteriophage may be labeled. The progeny bacteriophage released upon lysis of the bacteria (and in some cases the progeny and the infecting bacteriophage) may then be isolated from the sample by pumping the sample via third container 9 into a detector 10. At this point, the progeny (e.g., labeled) bacteriophage may be detected by a detector 10 that can detect the incorporated label. For example, samples may be passed through the system at five minute intervals, or another appropriate rate, and collected at the end for measuring progeny infectious agents. In an embodiment, the unadsorbed infectious agents (i.e., unadsorbed parental phage) may be removed by rinsing prior to lysis of the bacteria. For example, the unadsorbed infectious agents will pass through the filter 8, but the bacteria will not.

Figure 2:
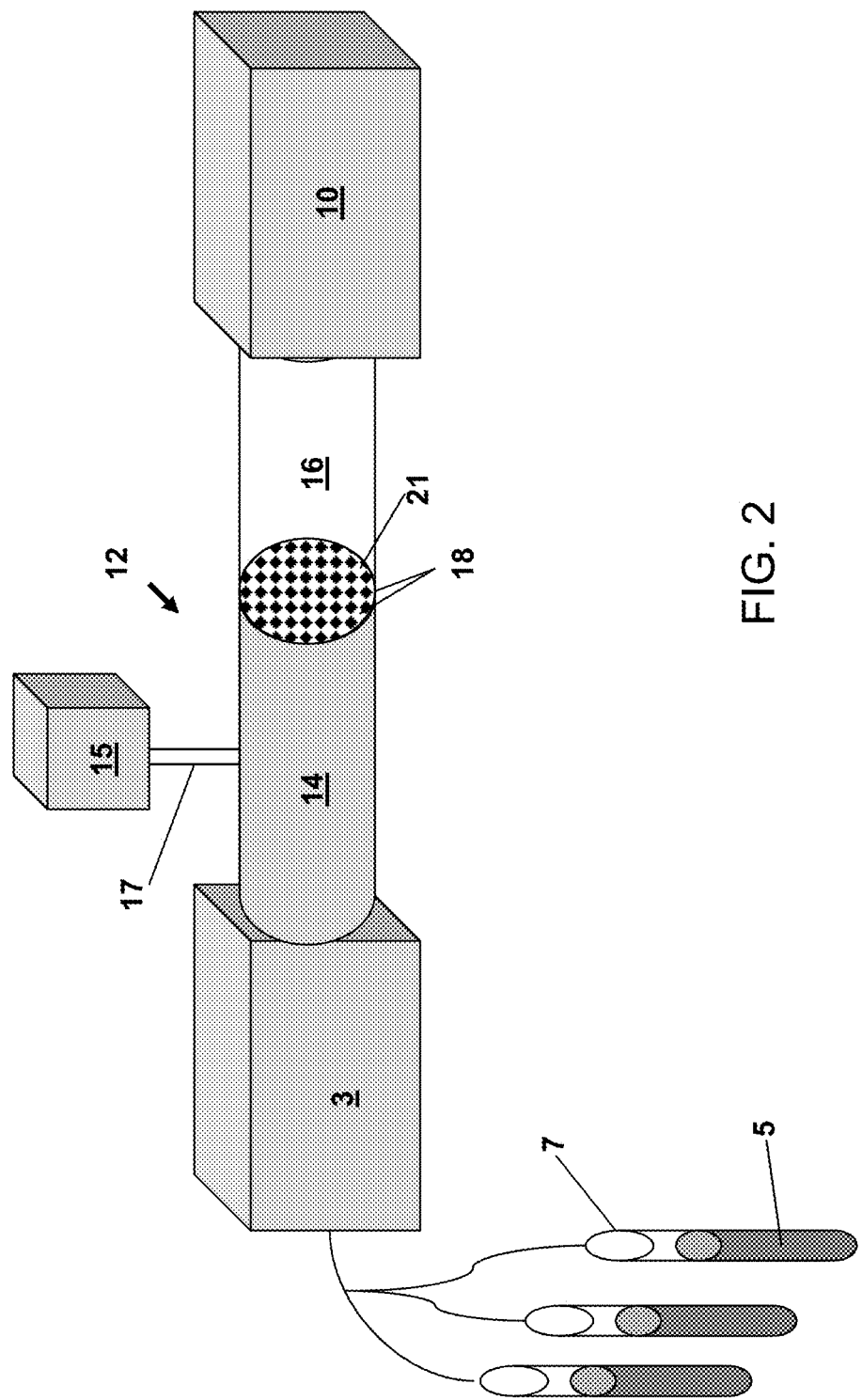
FIG. 2 illustrates a system for measuring bacteriophage in accordance with an alternate embodiment of the invention.

FIG. 2 shows an alternate embodiment of a device or system 12 of the invention. Again, the device or system may comprise a pump 3 that is used to transfer a biological sample 5 from a collection container 7 through the system. The device or system of the invention may comprise a first chamber 14 which will contain sample that is being transferred from the collection container 7 through the system. Upon entering the first chamber 14, the sample may be treated with an infectious agent, (e.g., bacteriophage) that can infect a host microorganism (e.g., bacteria) that is in the sample. For example, the infectious agent used to infect the microorganism in the sample may be stored in container 15 and introduced via port 17. Upon infection and replication, the progeny phage may be transferred to a smaller second chamber 16 via a porous membrane 18. The porous membrane may have holes 21 that are small enough to allow the bacteriophage to exit the chamber 14, but not let the bacteria (and other sample components) exit the chamber. The bacteriophage in the second chamber 16 could then be transferred to a detection chamber (i.e., detector) 10. Detection of the bacteriophage may be by immunoassay, luminescence, fluorescence (e.g., by detection of labeled precursor molecules incorporated into the bacteriophage), visually, or by other methods known in the art.

In certain embodiments, the device or system may comprise use of a binding agent (e.g., in the first chamber 14) that can bind the infectious agent that is used to infect the microorganism. In this way, the agent used to infect the microorganism can be separated from the progeny infectious agents that may be released from the microorganism upon lysis. For example, in certain embodiments, the bacteriophage in the first chamber 14 may be bound to a solid support. The bacteriophage bound to the solid support can then infect any bacteria in the sample, but will not pass through the pores 21 into a second chamber 16 for detection. In an embodiment, the unadsorbed infectious agents (i.e., unadsorbed parental phage) may be removed by rinsing prior to lysis of the bacteria. For example, the unadsorbed infectious agents will pass through the filter 18, but the bacteria will not.

Figure 3:
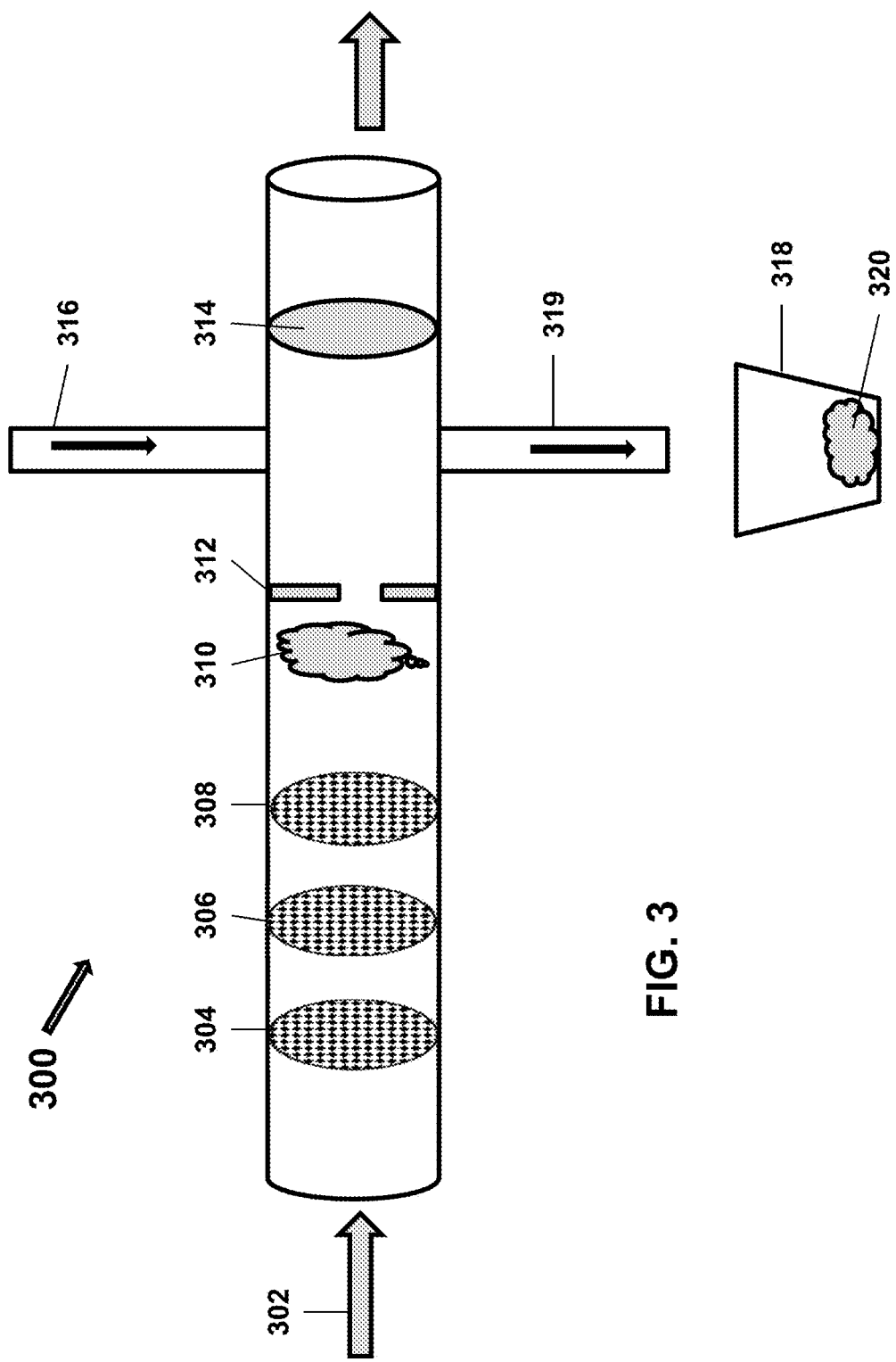
FIG. 3 illustrates a system for measuring bacteriophage in accordance with an alternate embodiment of the invention

FIG. 3 shows an alternate embodiment of such a device or system 300 where serial filters 304, 306 and 308 are used to purify a population of microorganisms of interest 310 away from other components in the sample as the sample flows 302 through the device. The filters may, in an embodiment, be serially decreased in pore size, such that first filter 304 has a larger pore size than second filter 306, which has a larger pore size than the next filter 308. Also, fewer or more serial filters may be used (e.g., the number of filters may range from 0 to 20 and anywhere in between). The device or system may comprise a pore 312 to prevent backwash (e.g., a back flow fence). Also, the system may comprise an inlet 316 for addition of an infectious agent. In an embodiment, the unadsorbed infectious agents (i.e., unadsorbed parental phage) may be removed (prior to lysis of the bacteria) by rinsing. For example, the unadsorbed infectious agents will pass through a filter 314, but the bacteria will not. Any progeny infectious agents may be allowed to flow through a small micron filter (e.g., 0.22 µm) for subsequent measurement. The lysed bacteria 320 may be removed by outlet 319 and captured in container 318.

As noted above, methods of separation of the progeny infectious agents and the infecting infectious agents may be used. For example, where biotinylated phage are bound to a streptavidin magnetic bead, the infecting bacteriophage may be sequestered by using a magnet to sequester and remove the infecting bacteriophage from the sample so as to allow for measurement of the resultant progeny bacteriophage. In an embodiment the phage is linked to an immobilized binding agent such as, but not limited to: streptavidin; biotin; an antibody that specifically binds to the bacteriophage or to a bacteriophage substructure, such as the head of the bacteriophage.

In addition to the measurement of a labeled precursor biomolecule that becomes incorporated, whether an infectious agent has infected a microorganism of interest can be determined by an assay that can identify the presence of progeny infectious agents or a biomolecule released from the infectious agents (e.g., phage) or host upon infection (e.g., a biomarker). Detection of biomolecules is described in more detail herein. In an embodiment, the assay not only can identify the progeny infectious agents or the biomolecule, but also the quantity or concentration of the progeny infectious agents or the biomolecule.

For example, the detection chamber used in the devices or systems of the invention may comprise antibodies to the progeny infectious agent (e.g., bacteriophage) that are immobilized on a membrane or other solid surface. Or, the detection chamber of the devices and systems of the invention may comprise a protein that binds to the progeny infectious agents wherein the binding protein is immobilized on a membrane or other solid surface. Binding of the progeny infectious agents to the antibodies and/or other binding protein may allow for a signaling mechanism to occur. For example, in one embodiment, binding of the progeny infectious agents to a primary antibody may allow for binding of a secondary antibody to the primary antibody, where the second antibody comprises a signaling mechanism (e.g., such as a fluorescent label). Or, binding of the progeny infectious agents to a binding protein may allow for binding of a primary antibody to the infectious agent, where the primary antibody comprises a signaling mechanism (e.g., such as a fluorescent label) or can bind to a secondary antibody with a signaling mechanism.

Or, detection of the progeny infectious agents may employ other signaling mechanisms. For example, in one embodiment and as described in more detail herein, binding of the progeny infectious agents to a protein that recognizes the progeny infectious agents may trigger an electrical signal that can be monitored and quantified. For example, in some embodiments, the progeny infectious agents may be bound to a protein that exhibits a conformational change or a chemical change (e.g., release of an ion) upon binding of the progeny infectious agents. This chemical and/or conformational change may then provide a change in electrical current that can be measured. For example, in one embodiment, release of an ion could change the electrical potential across a membrane in the second chamber to allow for detection of progeny infectious agents binding to a protein.

In some embodiments, the microorganism is a bacteria and the infectious agent is a bacteriophage. As described above, bacteriophage are viruses that attach to particular bacteria and inject its genetic material. The bacteriophage then uses the machinery of the bacteria to replicate itself tens of thousands of times in a short time period. Some bacteriophage are lytic, meaning that they rupture the host bacteria and the replicated phage (progeny) are released into the environment in order to seek out and infect other bacteria. Additionally, some bacteriophage are specific to particular bacteria, that is, replication of a particular bacteriophage only occurs in specific bacteria. Therefore, the presence of an amplified population of bacteriophage is then also an indication of the presence of the bacteria to which it is specific. Further, since bacteriophage can infect a bacterium and produce progeny phage in as little as an hour or less, the detection time is significantly reduced.

The total reaction time for phage infection of a bacterium, phage multiplication, or amplification in the bacterium, through lysing of the bacterium may take anywhere from tens of minutes to hours, depending on the phage and bacterium in question and the environmental conditions. Once the bacterium is lysed, progeny phage are released into the environment along with all the contents of the bacteria. The progeny phage can infect other bacteria that are present, and repeat the cycle to create more phage and more bacterial debris. In this manner, the number of phage will increase exponentially until there are essentially no more bacteria to infect.

Bacteriophage have the capability to exhibit specificity in addition to the ability to produce a substantial amount of progeny in a short period of time. Under optimum infection and host growth medium conditions, a given phage/bacterium combination gives rise to a consistent number of phage progeny. Generally, the lytic infection cycle produces 100 or more progeny phage particles from a single infected cell in about one hour. Within an assay it may be necessary to include control comparison standards, done in the same medium, with known numbers of phage infecting known numbers of substrate-bound target cells.

For the detection of a given bacterial cell, a bacteriophage that is capable of infecting the bacterial cell, replicating within the bacterial cell and lysing the bacterial cell may be selected. For any given bacterial cell a wide variety of bacteriophage are available, for example, from ATCC or by isolation from natural sources that harbor the host cells. The bacteriophage should also exhibit specificity for the bacterial cell. A bacteriophage is specific for a bacterial cell when it infects the given bacterial cell and does not infect bacterial cells of other species or strains. For the detection of a particular bacterial cell, one would also preferably select a bacteriophage that gives an optimal or maximal burst size.

Where a bacteriophage is used either for isolation of the bacteria, and/or amplification of detection of the bacteria as discussed below, the range of bacterial cells that can be detected by the present invention is limited only by the availability of a bacteriophage specific for the bacterial cell and will be realized to be vast by those skilled in the art. For example a list of phage types available from ATCC is published by them as the Catalogue of Bacteria & Bacteriophages and is available on the worldwide web at atcc.org. Other such depositories also publish equivalent data in their catalogues, and this may be used to identify possible bacteriophage reagents for the methods of the present invention.

Bacteriophages may be immobilized on a substrate by one of many procedures known in the art. For example, an antibody specific for the bacteriophage may be used to attach a bacteriophage to a substrate such as, but not limited to, a bead. Alternatively, protein A, protein G, or ligands, such as avidin, streptavidin and biotin, may be used. Covalent linkage methods may also be used to attach a bacteriophage to a substrate. Generally, antibodies with a specificity for bacteriophage tail proteins should not be used, as the binding of such an antibody to the tail proteins can interfere with the ability of the bacteriophage particle to bind to a host bacterial cell.

Substrates that may be used to bind a bacteriophage include, but are not limited to, plain polystyrene or magnetic beads (Spherotech, Libertyville, Ill.; Invitrogen; Polyscience, Niles, Fla.; Thermo Scientific Pierce; Millipore; New England Biolabs), magnetic beads (Dynal Biotech, Lake Success, N.Y.), plain or magnetic silica beads (AmsBio, Lake Forest, Calif.), latex coatings, a membrane filter, a fiber filter, a free fiber, or a porous solid substrate. Methods for the use of magnetic beads can be found, for example, with the package insert of Dynabeads Protein G Prod. No. 10003D, in Kala et al., Analytical Biochemistry 254:263-266 (1997) and in Dutton, Genetic Engineering News, Volume 22, Number 13, July 2002.

The presence of progeny bacteriophage isolated from a microorganism may also be determined by other methods well known in the art. For example, progeny bacteriophage may be detected by conventional plaque assay methods or by automated technologies, including, for example, cell sorters, such as fluorescent activated cell sorting (FACS).

Progeny bacteriophage may also be detected by direct visualization (Anderson et al., (US 2004/0137430, the disclosure of which is incorporated by reference herein). Such direct visualization may utilize light or fluorescence microscopy. Stains or enzymes that may be used include, but are not limited to, the fluorescent probe Alexa Fluor (available from Life Technologies/Molecular Probes, Grand Island, N.Y.), CY3®, fluorescein isothiocyanate, tetramethylrhodamine, horseradish peroxidase, alkaline phosphatase, glucose oxidase or any other label known in the art. Alternatively, a laser system may be used to detect labeled bacteriophage. Other detection methods include the detection of adenylate kinase, see Murphy et al., pp. 320-322 of Bioluminescence and Chemiluminesence in Medicine and Disease, Clinical Chemistry and Microbiology, and detection using a binomial-based bacterial ice nucleation detection assay, see Irwin et al., Journal of AOAC International 83:1087-95 (2000). Or, for some embodiments, progeny bacteriophage may also be detected by methods utilizing bioluminescence, detecting the expression of a luciferase gene cloned into the bacteriophage genome. See, for example, Loessner et al., Applied and Environmental Microbiology 62(4):1133-1140 (1996).

Also, QUANTUM DOTS ("QDOTS®") nanocrystals, manufactured by Life Technologies/Molecular Probes may be used in the methods of the present invention to detect immunocomplexes, e.g., as for detection of phage proteins released from bacterial cells. QDOTS® are nanoscale crystals that exhibit a number of favorable characteristics over conventional fluorescent dyes. Unlike fluorescent dyes, QDOTS® nanocrystals photobleach much more slowly and fluoresce much more brightly. Because of the array of different sizes available, QDOTS® nanocrystals cover a broader optical spectrum (i.e., different sizes emit different colors), thereby allowing for the detection of different organisms in the same sample. QDOTS® nanocrystals are manufactured with the same uniform conjugational chemistry, thereby providing consistent behavior under multiple assay environments. Currently, QDOTS® nanocrystals are available as several different conjugates, including streptavidin, protein A, and biotin. In some embodiments of the present invention, streptavidin conjugates may be used to fluoresce progeny infectious agents (e.g., bacteriophage) or their constituent proteins via a QDOT®-streptavidin-biotin-antibody complex. The streptavidin conjugates are extremely bright, provide excellent photostability, and have a single excitation source.

Detection of Biomolecules

Certain embodiments of the invention comprise devices, systems and methods for the detection of biomolecules. For example, in one embodiment, the invention comprises detection of biomolecules released from microorganisms. Thus, each of the methods, devices and systems described herein may comprise a component for detection of a biomolecule of interest.

Thus, in an embodiment, the invention comprises a device or system for detection of a biomolecule comprising: a container for holding at least one recognition partner for the biomolecule, wherein the recognition partner undergoes a measurable physical or chemical transformation upon interaction with the biomolecule; and a unit that detects the measurable physical or chemical transformation.

A variety of biomolecule analytes and recognition partners may be used. For example, the biomolecule may be a ligand for a receptor, and the recognition partner is the receptor. Or, the biomolecule may be transported across a cellular membrane, and the recognition partner may comprise a transport molecule in the membrane. In certain embodiments, the biomolecule may be a neurotransmitter, and the recognition partner is a neuron having receptors for the neurotransmitter. Or, the biomolecule may be an ion, and the recognition partner is a protein or other biomolecule that has a specific moiety (or moieties) that bind the ion.

A variety of measurable physical or chemical transformations may be detected. In an embodiment, the measurable physical or chemical transformation may comprise a change in pH. Or, the measurable physical or chemical transformation may comprise a change in electrical potential. Or, the measurable physical or chemical transformation may comprise a change in action potential across a neuron. In yet other embodiments, the measurable physical or chemical transformation may comprise a change in protein conformation.

In various embodiments, the measurable physical or chemical transformation is quantified. For example, the measurable physical or chemical transformation may be detected using a sensor. In certain embodiments, the measurable physical or chemical transformation is converted to a measurable signal, such as an electrical signal. The signal may be sent to a computer for further analysis and/or processing.

Figure 4:
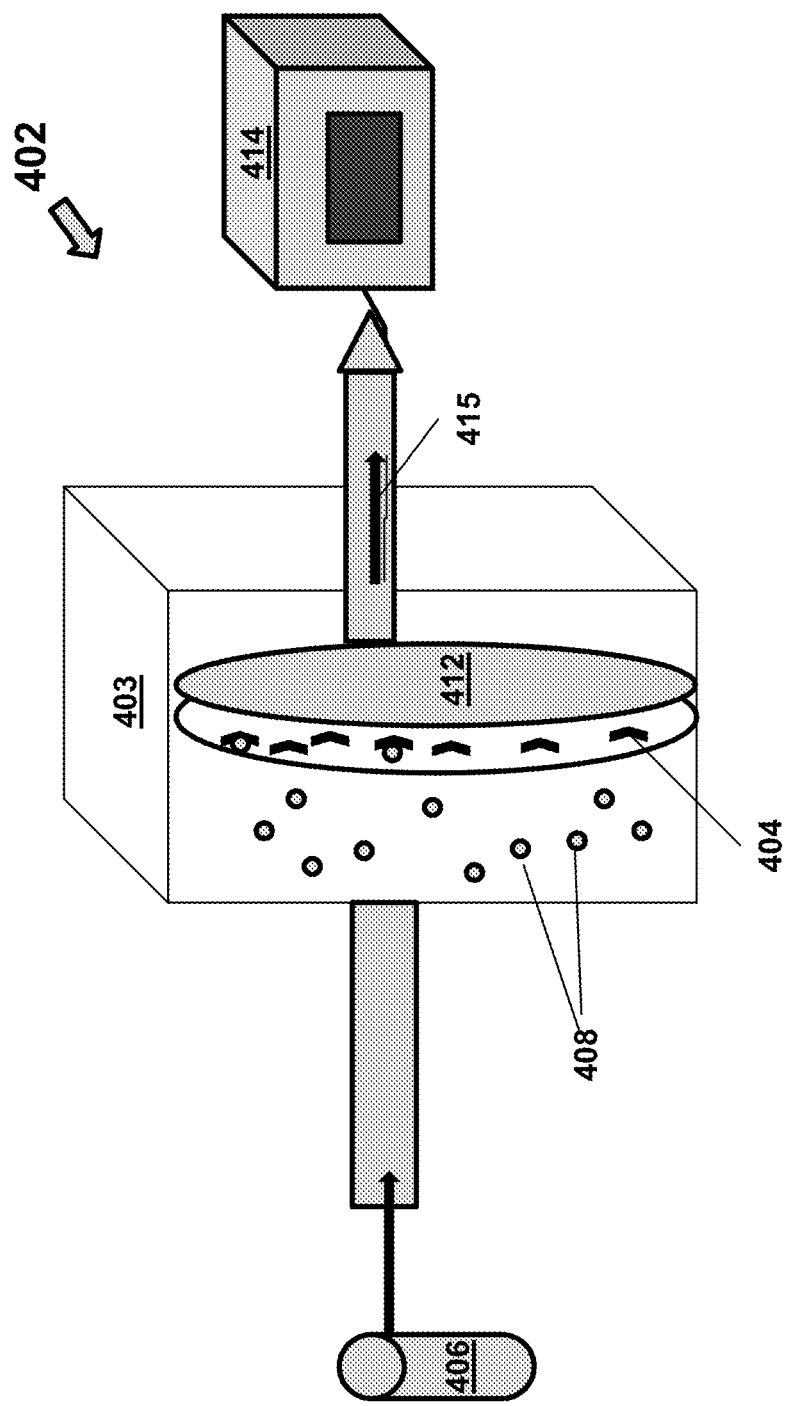
FIG. 4 illustrates a device for measuring a biomolecule in accordance with an embodiment of the invention.

Referring now to FIG. 4, in an embodiment, a device and/or system of the invention 402 may comprise a container 403 that contains a recognition partner 404 for a biomolecule of interest. For example, the container may comprise a network of cloned cells as the recognition partner for a biomolecule (e.g., analyte) of interest, such that when the analyte of interest binds to the cells, a change in voltage across either the cell membrane or the entire cell is generated. Thus, in an embodiment, the user may expose a biological sample 406 comprising an analyte of interest 408 to the recognition partner 404 in the container 403. Upon binding of the analyte of interest, the recognition partner (e.g., cell(s)) may generate a measurable physical or chemical transformation (e.g., an action potential which results in an electric current). The measurable physical or chemical transformation (e.g., current) may be detected via a sensor 412 and the signal 415 sent to a computer 414. The signal may be quantitated via the computer 414 or directly via the sensor. Also, the signal may be sent to a computer for further analysis, processing or saving of the data.

For example, in one embodiment, the device or system may comprise a hollow disk about 1 cm in diameter (or smaller) and containing a network of cells (e.g., neurons or astrocytes) which have receptors on their surfaces. When the cells encounter specific metabolites they would trigger an electrical reaction. The electrical reaction may then be measured using a microchip and sent wirelessly to a computer. In an embodiment, this type of device could measure glucose or sodium in a fraction of a second and would be the size of a wrist watch (or smaller).

Methods for Detection of Biomolecules

In certain embodiments, the invention comprises methods for measuring a biomolecule using the devices and/or systems of the invention.

Thus, in certain embodiments, the invention comprises a method for measuring a biomolecule using a device for detection of a biomolecule comprising: adding a sample comprising a biomolecule of interest to a container for holding at least one recognition partner for the biomolecule, wherein the recognition partner undergoes a measurable physical or chemical transformation upon interaction with the biomolecule; and measuring the physical or chemical transformation using a unit that detects the measurable physical or chemical transformation.

A variety of biomolecule analytes and recognition partners may be used. For example, the biomolecule may be a ligand for a receptor, and the recognition partner is the receptor. Or, the biomolecule may be transported across a cellular membrane, and the recognition partner may comprise a transport molecule in the membrane. In certain embodiments, the biomolecule may be a neurotransmitter, and the recognition partner is a neuron having receptors for the neurotransmitter. Or, the biomolecule may be an ion, and the recognition partner is a protein or other biomolecule that has a specific moiety (or moieties) that bind the ion.

A variety of measurable physical or chemical transformations may be detected. In an embodiment, the measurable physical or chemical transformation may comprise a change in pH. Or, the measurable physical or chemical transformation may comprise a change in electrical potential. Or, the measurable physical or chemical transformation may comprise a change in action potential across a neuron. In yet other embodiments, the measurable physical or chemical transformation may comprise a change in protein conformation.

In various embodiments, the measurable physical or chemical transformation is quantified. For example, the measurable physical or chemical transformation may be detected using a sensor. In certain embodiments, the measurable physical or chemical transformation is converted to a measurable signal, such as an electrical signal. The signal may be sent to a computer for further analysis and/or processing.

Figure 5:
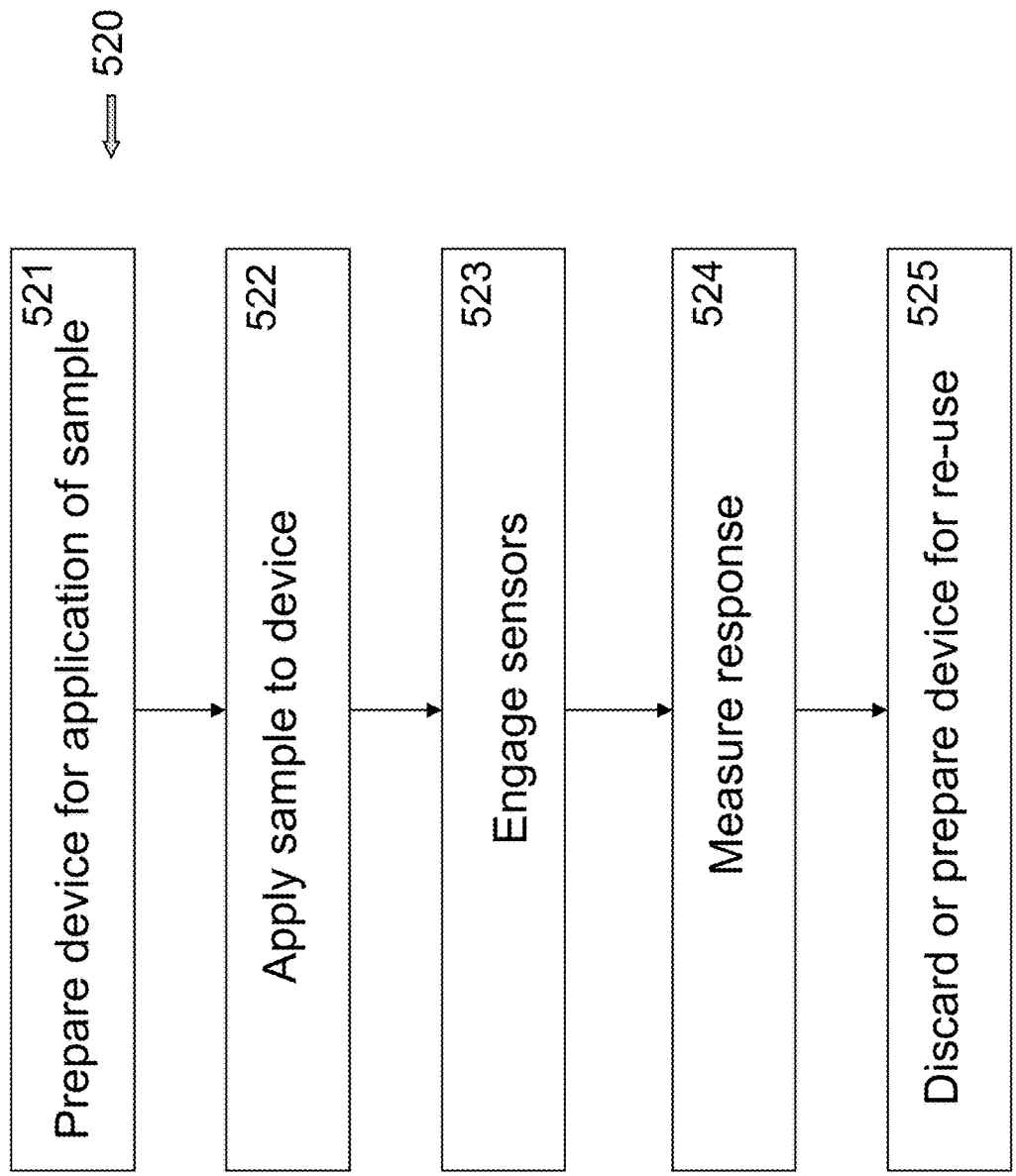
FIG. 5 illustrates a method for measuring a biomolecule using a device in accordance with an embodiment of the invention.

For example, as shown in FIG. 5, in one embodiment of the method 520, one prepares the device for application of the sample 521. Thus, in an embodiment, a solid support comprising a recognition partner for the biomolecule of interest could have a protective layer, that can be removed immediately prior to use. For example, where the sensor comprises a biological sensor (e.g., such as a neuronal network), any fluid on the upper surface of the cells can be gently removed, and if necessary the cells rinsed with buffer or another physiological solution.

Next, the sample comprising the biomolecule analyte of interest may be applied onto the surface of the solid support comprising a recognition partner 522. At this point, a signal may be generated and the sensor may be activated 523, and then the signal resulting from application of the biomolecule analyte of interest to the cells may be quantified 524. Upon detection of the measured signal, the device may optionally, be discarded in a bio-safe manner or prepared for reuse 525.

Systems for Detection of Microorganisms and Biomolecules

As noted herein, in certain embodiments, each of the methods and devices of the invention described herein may be coupled to a computer (i.e., either directly or wirelessly) so as to comprise a computerized method and/or system.

For example, the present invention may comprise a system for detection of a microorganism comprising: a component for containing a sample comprising a microorganism; a component for adding an infectious agent that can infect the microorganism so as to generate progeny infectious agents; a component for detecting the progeny infectious agents, wherein detection of the infectious agents indicates that the microorganism is present in the sample; and a computer.

In certain embodiments, the system may comprise a component for introducing the infectious agents into the sample so as to infect the microorganism. Thus, in certain embodiments, the component for introducing the infectious agent may comprise a plurality of pores, wherein the pore size allows the progeny infectious agents to pass through the pore, but does not allow the microorganism to pass out through the pore.

In certain embodiments, the system may comprise a component for separating the progeny infectious agents from the infected microorganism. For example, in an embodiment, the separating component may comprise a sized-based separation component. Thus, in certain embodiments, the separating component may comprise filtration of the progeny infectious agents through a pore, wherein the pore size allows the progeny infectious agents to pass through the pore, but does not allow the microorganism to pass through the pore.

The system may employ a variety of detectors to detect the progeny infectious agents. In an embodiment, the detection component may comprise a container for holding at least one recognition partner for the biomolecule, wherein the recognition partner undergoes a measurable physical or chemical transformation upon interaction with the biomolecule; and a unit that detects the measurable physical or chemical transformation. For example, in an embodiment, the detection component provides for visual detection of the progeny infectious agents, or detection of a label incorporated into the progeny infectious agents. Or, the detection component may provide for immunodetection of the infectious agent. Or, the detection component may provide an electrical or other quantifiable signal as discussed herein.

The system may also comprise a component for isolating any microorganisms that may be present in the sample from other components in the sample. For example, in an embodiment, the system may comprise a binding agent that recognizes and bind to the microorganism. In an embodiment, the binding agent may be bound to a solid support.

The systems of the invention may be used to assay samples for a variety of microorganisms. In certain embodiments, the microorganism is a bacteria and the infectious agent is a bacteriophage.

Additionally and/or alternatively, the invention may comprise a system for detection of a biomolecule comprising a container for holding at least one recognition partner for the biomolecule, wherein the recognition partner undergoes a measurable physical or chemical transformation upon interaction with the biomolecule; a unit that detects the measurable physical or chemical transformation; and a computer.

A variety of biomolecule analytes and recognition partners may be used. For example, the biomolecule may be a ligand for a receptor, and the recognition partner is the receptor. Or, the biomolecule may be transported across a cellular membrane, and the recognition partner may comprise a transport molecule in the membrane. In certain embodiments, the biomolecule may be a neurotransmitter, and the recognition partner is a neuron having receptors for the neurotransmitter. Or, the biomolecule may be an ion, and the recognition partner is a protein or other biomolecule that has a specific moiety (or moieties) that bind the ion.

A variety of measurable physical or chemical transformations may be detected. In an embodiment, the measurable physical or chemical transformation may comprise a change in pH. Or, the measurable physical or chemical transformation may comprise a change in electrical potential. Or, the measurable physical or chemical transformation may comprise a change in action potential across a neuron. In yet other embodiments, the measurable physical or chemical transformation may comprise a change in protein conformation.

In various embodiments, the measurable physical or chemical transformation is quantified. For example, the measurable physical or chemical transformation may be detected using a sensor. In certain embodiments, the measurable physical or chemical transformation is converted to a measurable signal, such as an electrical signal. The signal may be sent to a computer for further analysis and/or processing.

Figure 6:
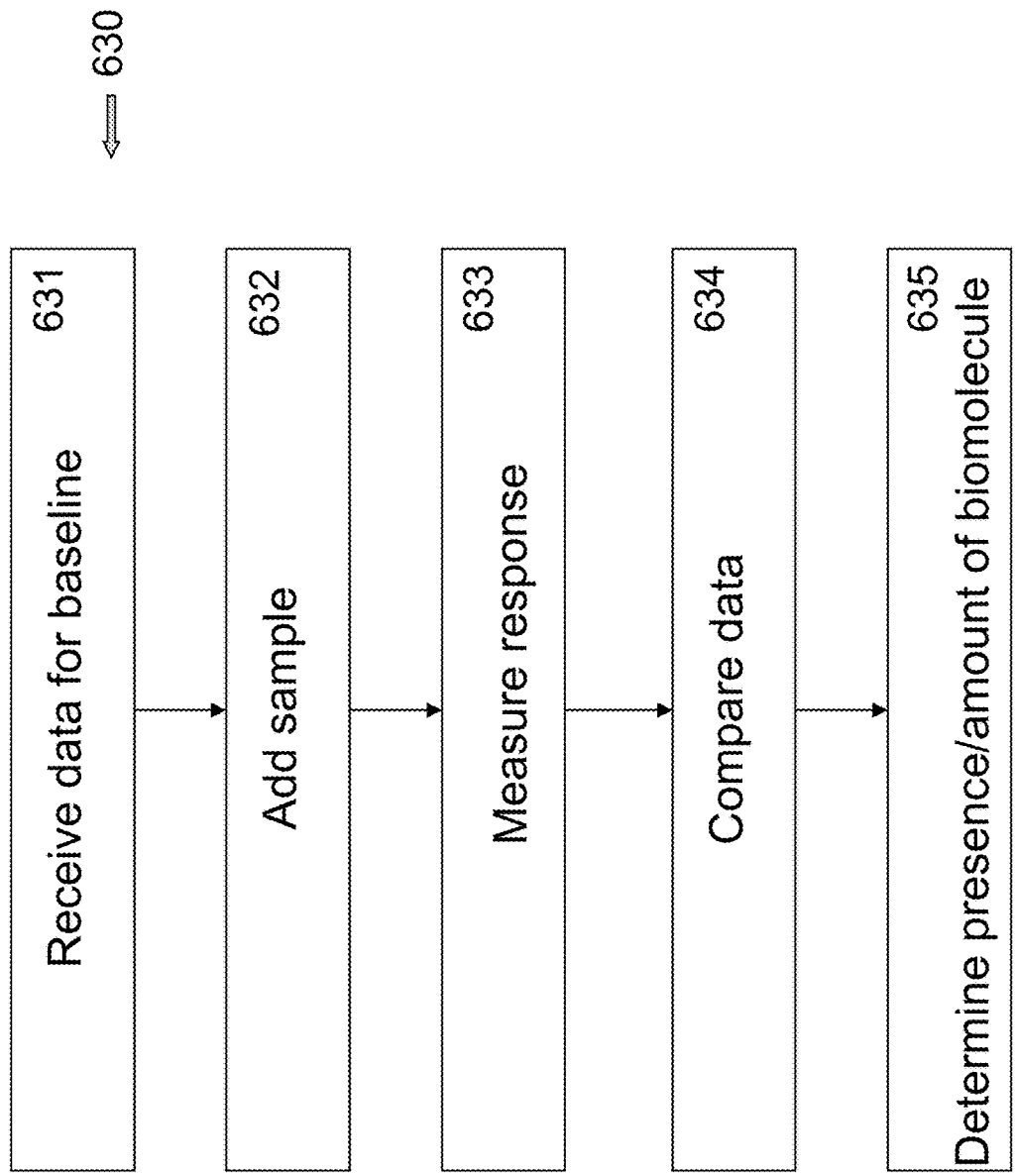
FIG. 6 illustrates a flow chart directed to a method of measuring a biomolecule according to an embodiment of the invention.

FIG. 6 illustrates a flow chart of one embodiment of a method 630 of using a computer-based system to measure a biomolecule from a microorganism using a device of the invention. The method shown in FIG. 6 can be further understood with respect to the system shown in FIGS. 7A and 7B and the electronic device shown in FIGS. 8A and 8B.

In the embodiment shown in FIG. 6, the invention provides a method 630 for determining the presence (or amount) of a biomolecule of interest, the method comprising: determining the baseline signal (i.e., prior to application of the sample) 631; adding the sample 632; measuring the response of the recognition partner upon application of the sample 633; comparing the baseline activity of the recognition partner to the response after application of the sample 634; and determining the presence and optionally, the amount of the biomolecule based on the measured signal 635.

FIGS. 7A and 7B show embodiments of illustrative systems suitable for executing one or more of the methods disclosed herein. For example, FIGS. 7A and 7B show diagrams depicting illustrative computing devices in illustrative computing environments according to some embodiments of the invention. The system 740 shown in FIG. 7A includes a device 703 comprising a sensor 712 providing data regarding the biomolecule of interest. The sensor 712 can interact with a computing device 741, a network 742, and a data store 743. The computing device 741 and the data store 743 are connected to the network 742. In this embodiment, the computing device 741 can communicate with the data store 743 through the network 742. Or, as shown in FIG. 7B, the computing device 41 may interact directly with data store 743.

As noted above, the system 740 may include a computing device 741. A suitable computing device for use with some embodiments may comprise any device capable of communicating with a network, such as network 742, or capable of sending or receiving information to or from another device, such as data store 743. A computing device can include an appropriate device operable to send and receive requests, messages, or information over an appropriate network. Examples of such suitable computing devices include personal computers, cell phones, handheld messaging devices, laptop computers, tablet computers, set-top boxes, personal data assistants (PDAs), servers, or any other suitable computing device. In some embodiments, the computing device 741 may be in communication with other computing devices directly or through network 742, or both. For example, in FIG. 7B, the computing device 741 is in direct communication with data store 743, such as via a point-to-point connection (e.g. a USB connection), an internal data bus (e.g. an internal Serial ATA connection) or external data bus (e.g. an external Serial ATA connection). In one embodiment, computer device 741 may comprise the data store 743. For example, in one embodiment, the data store 743 may comprise a hard drive that is a part of the computer device 741.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

As shown in FIG. 7A, in certain embodiments, the network 742 may facilitate communications between the computing device 741 and the data store 743. The network 742 may be any suitable number or type of networks or links, including, but not limited to, a dial-in network, a local area network (LAN), wide area network (WAN), public switched telephone network (PSTN), the Internet, an intranet or any combination of hard-wired and/or wireless communication links. In one embodiment, the network 742 may be a single network. In other embodiments, the network 742 may comprise two or more networks. For example, the computing device 741 may be connected to a first network and the data store 743 may be connected to a second network and the first and the second network may be connected. In one embodiment, the network 742 may comprise the Internet. Components used for such a system can depend at least in part upon the type of network and/or environment selected. Protocols and components for communicating via such a network are well known and will not be discussed herein in detail. Communication over the network can be enabled by wired or wireless connections, and combinations thereof. Numerous other network configurations would be known to a person of ordinary skill in the art.

As shown in both FIGS. 7A and 7B, the system 740 may, in certain embodiments, include a data store 743. The data store 743 can include several separate data tables, databases, or other data storage mechanisms and media for storing data relating to a particular aspect. It should be understood that there can be many other aspects that may need to be stored in the data store, such as to access right information, which can be stored in any appropriate mechanism or mechanisms in the data store 743. The data store 743 may be operable to receive instructions from the computing device 41 and obtain, update, or otherwise process data in response thereto.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device, e.g., a modem, a network card (wireless or wired), an infrared communication device, and/or working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

Figure 8B:
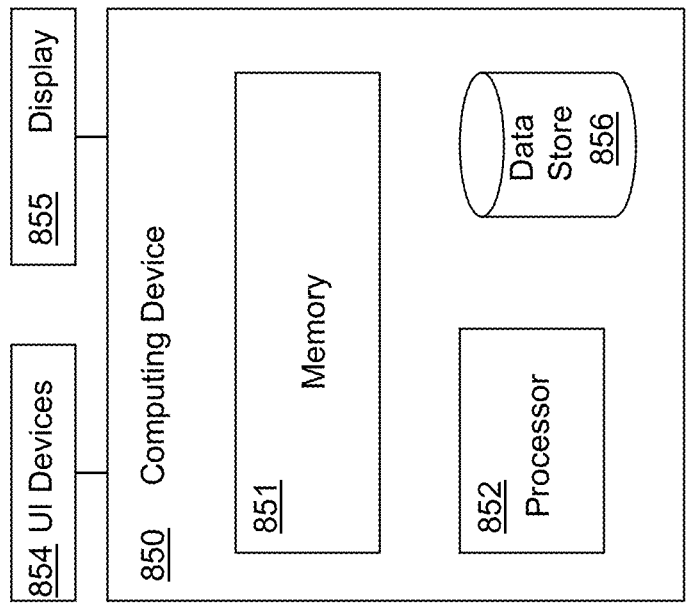
FIGS. 8A and 8B illustrate block diagrams depicting exemplary computing devices according to various embodiments of the invention.
Figure 8A:
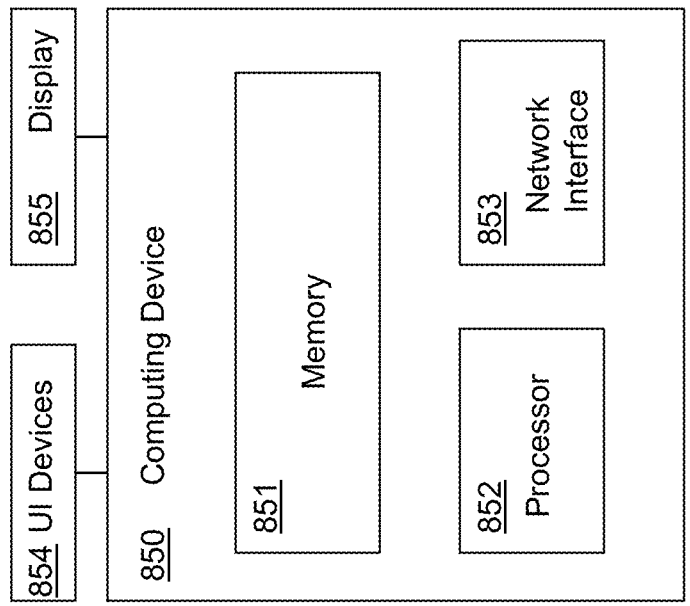

FIGS. 8A and 8B show block diagrams depicting exemplary computing devices according to various embodiments. According to the embodiments shown in FIGS. 8A and 8B, the computing device 850 may comprise a computer-readable medium such as memory 851 coupled to a processor 852 that is configured to execute computer-executable program instructions (or program code) and/or to access information stored in memory 851. A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, CAM, DDR, flash memory such as NAND flash or NOR flash, an ASIC, a configured processor, optical storage, magnetic tape or other magnetic storage, or any other medium from which a computer processor can read instructions. In one embodiment, the computing device 850 may comprise a single type of computer-readable medium such as random access memory (RAM). In other embodiments, the computing device 850 may comprise two or more types of computer-readable medium such as random access memory (RAM), a disk drive, and cache. The computing device 850 may be in communication with one or more external computer-readable mediums such as an external hard disk drive or an external DVD drive.

As discussed above, the computing device may comprise a processor 852 which is configured to execute computer-executable program instructions and/or to access information stored in memory 851. The instructions may comprise processor-specific instructions generated by a compiler and/or an interpreter from code written in any suitable computer-programming language including, for example, C, C++, C#, Visual Basic, Java, Python, Perl, JavaScript, and Action- Script®. In an embodiment, the computing device 50 comprises a single processor 52. In other embodiments, the device 850 comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device 850 may in certain embodiments also comprise a network interface 853 (e.g., FIG. 8A). In some embodiments, the network interface 53 is configured for communicating via wired or wireless communication links. For example, the network interface 53 may allow for communication over networks via Ethernet, IEEE 802.11 (Wi-Fi), 802.16 (Wi-Max), Bluetooth, infrared, etc. As another example, network interface 53 may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. Also, in some embodiments, such as the embodiment shown in FIG. 8B, the computing device may include a data store 56 in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device 850 shown in FIGS. 8A and 8B are in communication with various user interface (UI) devices 54 and a display 855. Display 855 may use any suitable technology including, but not limited to, LCD, LED, CRT, and the like.

In various embodiments, suitable computing devices may be a server, a desktop computer, a personal computing device, a mobile device, a tablet, a mobile phone, or any other type of electronic devices appropriate for providing one or more of the features described herein. In at least one aspect, the invention provides systems for carrying out the analysis described above. Thus, in some embodiments, the present invention comprises a computer-readable medium on which is encoded programming code for the detection and/or quantification of biomarkers. Also in some embodiments, such as described above with respect to FIGS. 7 and 8, the invention comprises a system comprising a processor in communication with a computer-readable medium, the processor configured to perform the generalized ridge regression methods described herein. Suitable processors and computer-readable media for various embodiments of the present invention are described in greater detail above.

Thus, in certain embodiments, the invention comprises a system for detection of a biomarker comprising: a sensor (or data provided from a sensor); and a processor in communication with the sensor, the processor configured to determine the presence of and/or the amount of a biomarker in a sample. The processor may, in certain embodiments, be further in communication with a database comprising data relating to prior biomarker measurements (e.g., a standard curve) or other data required for the calculation.

In other embodiments, the invention comprises a computer readable medium on which is encoded program code for detection of and/or quantification of a biomarker using a device and/or system of the invention.

Thus, in an embodiment, the starting point may comprise data generated from a data base of assays for the biomarker of interest. Once the data has been collected, it may be compiled and/or transformed if necessary using any standard spreadsheet software such as Microsoft Excel, FoxPro, Lotus, or the like. In an embodiment, the data are entered into the system for each experiment. Alternatively, data from previous runs are stored in the computer memory and used as required.

At each point in the analysis, the user may input instructions via a keyboard, floppy disk, remote access (e.g., via the internet), or other access means. The user may enter instructions including options for the run, how reports should be printed out, and the like. Also, at each step in the analysis, the data may be stored in the computer using a storage device common in the art such as disks, drives or memory. As is understood in the art, in certain embodiments, the processor and IU device (e.g., I/O controller) may be required for multiple aspects of computer function. Also, in an embodiment, there may be more than one processor.

The data may also be processed to remove noise. In some cases, the user, via the keyboard or remote access, or other means known in the art may want to input variables or constraints for the analysis, as for example, the threshold for determining noise.

In the next step, quantification of the biomarker may be performed. The results of the analysis may then be compiled and provided in a form for review by a user.

Samples

Each of the embodiments of the methods and systems of the invention can allow for the rapid detection and quantification of microbes in a sample. For example, methods according to the present invention can be performed, in less than about ten hours to less than about twelve hours, more preferably in less than about four hours to less than about three hours, and most preferably, in about two hours or less.

Microbes detected by the methods and systems of the present invention include pathogens that are of commercial, medical or veterinary concern. Such pathogens include Gram-negative bacteria, Gram-positive bacteria, mycoplasmas and viruses. Any microbe for which a binding agent that is specific for the particular microbe has been identified can be detected by the methods of the present invention. Those skilled in the art will appreciate that there is no limit to the application of the present methods other than the availability of the necessary specific binding agent/microbe pairs.

Bacterial cells detectable by the present invention include, but are not limited to, bacterial cells that are food or water borne pathogens. Bacterial cells detectable by the present invention include, but are not limited to, all species of *Salmonella*, all species of *Escherichia coli*, including, but not limited to *E. coli* O157/H7, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis*, *Camplyobacter jejuni*, *Chlamydia pneumoniae*, *Clostridium perfringens*, *Enterobacter* spp., *Klebsiella pneumoniae*, *Mycoplasma pneumoniae*, *Salmonella typhi*, *Shigella sonnei*, *Staphylococcus aureus*, and *Streptococcus* spp.

The sample may be environmental or food or water samples or medical or veterinary samples. Samples may be liquid, solid, or semi-solid. Samples may be swabs of solid surfaces. Samples may include environmental materials, such as the water samples, or the filters from air samples, or aerosol samples from cyclone collectors. Samples may be of meat, poultry, processed foods, milk, cheese, or other dairy products. Medical or veterinary samples include, but are not limited to, blood, sputum, cerebrospinal fluid, and fecal samples and different types of swabs.

Samples may be used directly in the detection methods of the present invention, without preparation or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to Na$^+$, Mg$^{2+}$, and K$^+$. Preferably a sample is maintained at a temperature that maintains the viability of any pathogen cells contained within the sample.

Preferably throughout detection assays, the sample is maintained at a temperature that maintains the viability of any pathogen cell present in the sample. For example, during steps in which an infectious agent (e.g., bacteriophage) are attaching to or infecting a microorganism of interest (e.g., bacterial cells), it is preferable to maintain the sample at a temperature that facilitates such infection and/or attachment. During steps in which infectious agents (e.g., bacteriophage) are replicating within an infected microorganism (e.g., bacterial cell) or lysing such an infected cell, it is preferable to maintain the sample at a temperature that promotes replication and lysis of the host. Such temperatures are at least about 25 degrees Celsius (C), more preferably no greater than about 45 degrees C., most preferably about 37 degrees C. It is also preferred that the samples be subjected to gentle mixing or shaking during bacteriophage attachment, replication and cell lysis. In other embodiments, the phage assembly may be inhibited after infection such that the subunits of the phage proteins accumulate unassembled and can provide an additional amplification of the progeny phage.

Assays may include various appropriate control samples. For example, control samples containing no bacteriophage or control samples containing bacteriophage without bacteria may be assayed as controls for background levels.

Kits for Detection of Microorgansims

Embodiments of the invention also comprise systems (e.g., kits) for performing the methods of the invention.

In an embodiment, the kit may comprise a device of the invention. In alternate embodiments, the kits may comprise reagents for isolation of the microorganism of interest from a sample and or precursor biomolecules that allow for detection of progeny microorganisms.

In alternate embodiments, the kit may comprise a specific infectious agent linked to an immobilized binding agent such as, but not limited to: streptavidin; biotin; an antibody that specifically binds to the infectious agent. In an embodiment, the infectious agent may be bound, via the binding agent to a solid support.

For example, the kit may comprise a specific phage linked to an immobilized binding agent such as, but not limited to: streptavidin; biotin; an antibody that specifically binds to the bacteriophage or to a bacteriophage substructure, such as the head; an isolated viral receptor protein; or a cell that is capable of being infected by the bacteriophage. In an embodiment, the agent linked to the bacteriophage is used to link the phage to a solid support. For example, in one embodiment, the kit may comprise a biotinylated phage specific for a bacterium of interest. In this way, the biotinylated phage can be bound to a streptavidin magnetic bead.

In alternate embodiments, bacteriophage, phage, mycobacteriophage (such as for TB and paraTB), mycophage (such as for fungi), *mycoplasma* phage, or mycoplasmal phage, and any other virus that can invade living bacteria, fungi, mycoplasmas, protozoa, yeasts, and other microscopic living organisms can be coupled to a solid support for isolation of a microbe of interest. As an example, well-studied phage of *E. coli* include T1, T2, T3, T4, T5, T7, and lambda; other *E. coli* phage available in ATCC collection include phiX174, S13, Ox6, MS2, phiV1, fd, PR772, and ZIK1.

Any of the commercially available phage may be used to generate reagents for the kits of the invention. For example a list of phage types available from ATCC is published by them as the Catalogue of Bacteria & Bacteriophages and is available on the worldwide web at atcc.org. or other known depositories.

Infectious agents may be immobilized on a substrate by one of many procedures known in the art. For example, an antibody specific for the infectious agent (e.g., bacteriophage) may be used to attach an infectious agent to a substrate. Protein A, protein G, or ligands such as avidin, streptavidin, and biotin, may be used to link the antibody to the substrate. Covalent linkage methods may also be used to attach an infectious agent (e.g. bacteriophage) to a substrate. Generally, antibodies with specificity for bacteriophage tail proteins should not be used, as the binding of such an antibody to the tail proteins can interfere with the ability of the bacteriophage particles to bind to a host bacterial cell.

Substrates to be used in the kits of the present invention include, but are not limited to, polystyrene beads (Spherotech, Libertyville, Ill.), magnetic beads (Life Technologies/Invitrogen; AmsBio), latex coatings, a membrane filter, a fiber filter, a free fiber, or a porous solid substrate. Methods for the use of magnetic beads can be found, for example, with the package insert of Dynabeads Protein G Prod. No. 10003/D, in Kala et al., Analytical Biochemistry 254:263-266 (1997) and in Dutton, Genetic Engineering News, Volume 22, Number 13, July 2002.

A wide spectrum of particles, particularly magnetic and polystyrene beads, is commercially available in a wide range of sizes. For certain embodiments, a preferred set of particles has an average particle size (i.e., the largest dimension of the particles) of about one micrometer (i.e., micron). For certain embodiments, a preferred set of particles has an average particle size (i.e., the largest dimension of the particles) of no less than 10 micrometers (i.e., microns). Exemplary commercially available beads are protein G-, protein A-, and proteins A/G-coated polystyrene beads and streptavidin-coated polystyrene beads that are available from Invitrogen, Carlsbad, Calif. or from Spherotech, Libertyville, Ill. Other suppliers of polystyrene and magnetic beads include Thermo Scientific Pierce, Millipore, Polyscience, and New England Biolabs. AmsBio, Lake Forest, Ill. is a supplier of magnetic silica beads, which are available with all of the protein coatings given above. Invitrogen also supplies epoxy surface magnetic beads, which bind antibodies covalently.

The kits may also comprise secondary antibodies that can be used to detect the primary antibodies, where such antibodies may be anti-globulin antibodies from a second species. These antibodies may be labeled with a detectable marker or a binding agent that can complex with a detectable marker. For example, in certain embodiments, a kit of the invention may comprise a secondary antibody that is bound to a fluorophore. In an embodiment, the fluorophore may comprise a QDot. For example, in one embodiment, streptavidin-QDots can be bound to biotinylated secondary antibodies that recognize, e.g., a primary antibody.

While the preferred embodiments of the invention have been illustrated and described, it will be appreciated that various changes can be made therein without departing from the spirit and scope of the invention. All printed patents and publications referred to in this application are hereby incorporated herein in their entirety by this reference.

That which is claimed is:

1. A method for detecting a microorganism in a sample, comprising:
    infecting the microorganism with a lytic bacteriophage capable of infecting the microorganism to generate progeny bacteriophage and a soluble enzyme released when the microorganism is lysed by the progeny bacteriophage;
    allowing the infected microorganism to be lysed by the progeny bacteriophage; and,
    detecting a detectable product of a reaction catalyzed by the released soluble enzyme found in solution in the sample, wherein detection of the detectable product indicates that the microorganism is present in the sample.

2. The method of claim 1, wherein the soluble enzyme is a soluble luciferase.

3. The method of claim 1, wherein the microorganism is a bacterium.

4. The method of claim 1, wherein the detecting is performed by a detector configured to detect a detectable product.

5. The method of claim 4, wherein the detector is a luminescence detector.

6. The method of claim 4, wherein the detector is coupled directly or remotely to a computer.

7. The method of claim 1, further comprising separating the progeny bacteriophage from the infected microorganism.

8. The method of claim 7, wherein the separating comprises filtration of the progeny bacteriophage through a pore, wherein size of the pore allows the progeny bacteriophage to pass through the pore, but does not allow the microorganism to pass through the pore.

9. The method of claim 1, further comprising isolating the microorgansim from other components in the sample by binding of the microorganism to a binding agent.

10. The method of claim 9, wherein the binding agent is bound to a solid support.

11. A method for detecting a microorganism in a sample, comprising:
    contacting in a chamber the sample with a lytic bacteriophage capable of infecting the microorganism to generate progeny bacteriophage and a soluble enzyme released when the microorganism is lysed by the progeny bacteriophage;
    detecting by a detector a detectable product of a reaction catalyzed by the released soluble enzyme found in solution in the sample, wherein detection of the detectable product indicates that the microorganism is present in the sample.

12. The method of claim 11, wherein the soluble enzyme is a soluble luciferase.

13. The method of claim 11, wherein the microorganism is a bacterium.

14. The method of claim 11, wherein the detector is a luminescence detector.

15. The method of claim 11 wherein the detector is coupled directly or remotely to a computer.

16. The method of claim 11, further comprising separating the progeny bacteriophage from the infected microorganism prior to the detecting.

17. The method of claim 16, wherein the separating comprises filtration of the progeny bacteriophage through a pore, wherein size of the pore allows the progeny bacteriophage to pass through the pore, but does not allow the microorganism to pass through the pore.

18. The method of claim 11, further comprising isolating the microorganism from other components in the sample by binding of the microorganism to a binding agent in the chamber.

19. The method of claim 18, wherein the binding agent is bound to a solid support.

20. The method of claim 11, wherein the chamber comprises a binding agent that binds to the lytic bacteriophage.

21. The method of claim 20, wherein the binding reagent is bound to a solid support.

* * * * *